United States Patent [19]

Wu et al.

[11] Patent Number: 4,780,315

[45] Date of Patent: * Oct. 25, 1988

[54] RUMEN-STABLE PELLETS

[75] Inventors: Stephen H. W. Wu; Edward G. Miller, Jr., both of Kingsport, Tenn.

[73] Assignee: Eastman Kodak Company, Rochester, N.Y.

[*] Notice: The portion of the term of this patent subsequent to Jan. 2, 2005 has been disclaimed.

[21] Appl. No.: 802,105

[22] Filed: Nov. 25, 1985

[51] Int. Cl.$^4$ .......................... A61K 9/22; A61K 9/24
[52] U.S. Cl. ................................ 424/438; 424/462; 424/482; 524/394; 524/400; 524/451; 604/890; 604/892.1
[58] Field of Search ............... 604/890, 892; 424/33, 424/31, 462, 482, 438; 524/451, 394, 400

[56] References Cited

U.S. PATENT DOCUMENTS

| | | | |
|---|---|---|---|
| 3,041,243 | 6/1962 | Sagimoto et al. | 167/82 |
| 3,619,200 | 11/1971 | Ferguson et al. | 99/2 |
| 3,697,640 | 10/1972 | Grant et al. | 424/438 |
| 3,829,564 | 8/1974 | Merry et al. | 424/78 |
| 3,880,990 | 4/1975 | Bauer et al. | 424/438 |
| 4,117,801 | 10/1978 | Dannelly et al. | 118/20 |
| 4,177,255 | 12/1979 | Dannelly | 424/35 |
| 4,181,708 | 1/1980 | Dannelly | 424/438 |
| 4,181,709 | 1/1980 | Dannelly | 424/33 |
| 4,181,710 | 1/1980 | Dannelly et al. | 424/482 |
| 4,196,187 | 4/1980 | Dannelly et al. | 424/33 |
| 4,595,584 | 6/1986 | Wu et al. | 424/33 |

FOREIGN PATENT DOCUMENTS

| | | | |
|---|---|---|---|
| 77264 | 4/1983 | European Pat. Off. | |
| 188953 | 7/1986 | European Pat. Off. | |
| 57/122931 | 7/1982 | Japan | |
| WO84/282 | 2/1984 | PCT Int'l Appl. | 424/33 |
| 2170210 | 7/1986 | United Kingdom | 424/33 |
| WO84/4657 | 12/1984 | World Int. Prop. O. | |

*Primary Examiner*—Ronald W. Griffin
*Attorney, Agent, or Firm*—John F. Stevens; William P. Heath, Jr.

[57] ABSTRACT

Disclosed are rumen-stable compositions for coating medicaments and nutrients for ruminant animals. The coatings comprise a film-forming polymeric substance containing basic nitrogen groups, and an inorganic particulate material dispersed throughout the polymeric substance.

16 Claims, No Drawings

RUMEN-STABLE PELLETS

TECHNICAL FIELD

This invention relates in general to pellets adapted to be orally administered to ruminants and which are beneficial to ruminants after passing the rumen and reaching the abomasum and/or intestines. More particularly, this invention relates to pellets having, in terms of structure, a core material such as a nutrient or medicament, and a coating over the core material which protects the core in the environment of the rumen, but which loses continuity under the more acidic conditions of the abomasum and/or intestines to render the core material available for utilization by the animal.

BACKGROUND OF THE INVENTION

In ruminants, ingested feed first passes into the rumen, where it is pre-digested or degraded by fermentation. During this period of fermentation the ingested feed may be regurgitated to the mouth where it is salivated and masticated. After a period of fermentation regulated by natural processes and variables depending on the animal and the feedstuff, absorption of digested nutrients starts and continues in the subsequent sections of the digestive tract by the ruminant animal. This process is described in detail by D. C. Church, "Digestive Physiology and Nutrition of Ruminants", Vol. 1, Oregon State University Press.

The rumen, the largest of the four stomach compartments of ruminants, serves as an important location for metabolic breakdown of ingested foodstuffs through the action of microorganisms which are present therein. Ingested food is typically retained in the rumen for from about 6 to 30 hours during which time it is subject to metabolic breakdown by the rumen microorganisms. Much ingested protein material is broken down in the rumen to soluble peptides and amino acids and utilized by the rumen microorganisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH of about 5.5, so the active substance will be saved until it reaches the particular location where absorption takes place. It is well known that the rate of meat, wool and/or milk production can be increased if sources of growth limiting essential amino acids, and/or medicaments, are protected from alteration by microorganisms residing in the rumen and become available for direct absorption by the animal later in the gastrointestinal tract.

Materials which protect the core against degradation by the rumen contents should be resistant to attack by the rumen fluid which contains enzymes or microorganisms but must make the active ingredient available rapidly in the more acidic fluid of the abomasum at a pH within the normal physiological range of about 2 to about 3.5. To more easily coat or encapsulate active ingredients in protective materials, the protective materials should be soluble in certain organic solvents for coating purposes.

Because proteins are subject to breakdown in the rumen, it has been suggested that protein-containing nutrients fed to ruminants be treated so as to permit passage without microbial breakdown through the rumen to the abomasum. Suggested procedures have included coating the protein material, for example, with fats and vegetable oils; heat treating of the protein material; reacting the protein material with various compounds such as formaldehyde, acetylenic esters, polymerized unsaturated carboxylic acid or anhydrides and phosphonitrilic halides, etc.

It is well known that all proteins found in animal and plant life are chemical compounds containing different combinations of over 02 amino acids, the number and arrangement of such acids being fixed in any particular protein. Twelve of these amino acids can be synthesized in nutritionally adequate amounts from other substances by biochemical processing normally present in most animals, but the remaining 10 essential amino acids are not synthesized in sufficient quantities and must be ingested by the animal. Since the proportions of the constituent amino acids in a particular protein cannot be varied, the essential amino acid least in supply limits the amounts of that protein which can be produced by the animal. Consequently, for any given diet, there will be a particular essential amino acid which limits the production of protein incorporating that essential amino acid unless, of course, two or more such amino acids are equally limiting.

The application of the above principles leads to the formulation of diets for nonruminant animals which provide the optimum proportion of amino acids and have enabled significant increases in protein production to be achieved. In the ruminant, dietary proteins and amino acids are, to a variable extent, broken down to ammonia and various organic compounds by microbial fermentation in the first two compartments of the stomach (the rumen and reticulum). The bacteria and protozoa in these organs utilize these metabolites for their own growth and multiplication and the microbial protein so formed passes on to the abomasum, the compartment of the stomach corresponding to the stomach of nonruminants, where it is partially digested. The process is completed in the small intestine and the amino acids are absorbed.

It is likewise well-known that medicaments are more effective when they are protected from the environment of the rumen. See, for example, U.S. Pat. Nos. 3,041,243 and 3,697,640.

The need and the value of post-ruminal delivery of nutrients and pharamaceuticals by means of supplementing rumen-stable preparations in feed is discussed in a paper entitled, "Controlled-Release Additives for Ruminants: Cellullose-Based Coating Composition for Rumen-Stable Nutrients", by Wu, et al, in a book, *Controlled Release of Pesticides and Pharmaceuticals*, edited by D. H. Lewis, Plenum Press, New York, N.Y., 1981, p. 319.

The following patents by Dannelly, et al, teach the art of formulating rumen-stable coatings for a variety of nutrients and medicaments: U.S. Pat. Nos. 4,117,801; 4,177,255; 4,181,708; 4,181,709; 4,181,710; and 4,196,187.

U.S. Pat. No. 4,181,708 specifically teaches the ternary composition of a rumen-stable coating which comprises a polymeric material such as a copolymer of 2-methyl-5-vinylpyridine and styrene [copoly(2M5VP/ST)] which is resistant to mildly acidic environment of the rumen, and a hydrophobic substance of from about 5 to 50% of the polymer weight, and a flake material of from about 10 to 200% of the polymer weight dispersed throughout the continuous matrix. U.S. Pat. No. 4,181,709 specifically teaches the quaternary composition of a rumen-stable coating which comprises a polymeric material such as copoly(2M5VP/ST), a hydrophobic material of from about 2 to about 40% of the polymer weight, and a reactive fatty acid of from about 5 to about 40% of the polymer weight. U.S. Pat. No. 4,181,710 specifically teaches a binary composition of rumen-stable coating comprised of a polymeric matrix and a hydrophobic material being present in an amount between 5-50% of the polymer weight.

U.S. Pat. No. 4,177,255 specifically teaches a composition for a rumen stable coating which comprises a polymeric matrix which is resistant to acid and a substance dispersed therein which is leachable from the matrix in the environment of the abomasum but not the rumen.

Other patents of interest are as follows:

U.S. Pat. No. 3,619,200 relates to chemically modifying pellets and/or using a surface coating therefor. Various polymers are disclosed in this patent including copolymers of vinylpyridine and styrene. Canadian Pat. No. 911,649 discloses treatment of proeteinaceous materials with substances which are capable of reacting with proteins to form a polymeric proteinaceous complex on the surface of the material or by treating the proteinaceous material with a polymer or copolymer of a basic vinyl or acrylic monomer. This patent also discloses the use of copolymers and terpolymers derived from essentially a basic substituted acrylate or methacrylate monomer and at least one ethylenically unsaturated compound as rumen stable coatings. U.S. Pat. No. 3,880,990 and British Pat. No. 1,346,739 relate to an orally administratable ruminant composition where in a medicinal substance is encapsulated or embedded in a normally solid, physiologically acceptable basic polymer. The compositions are produced by dispersing a medicinal substance in a first solvent and adding thereto a second solvent which is miscible with the first solvent but in which the polymer and medicinal substance are substantially insoluble. U.S. Pat. No. 3, 041,243 relates to coatings for oral medicaments. These coatings are water-insoluble but acid-soluble film-forming polymers. An example mentioned in this patent is 2-methyl-5-vinylpyridine copolymerized with vinyl acetate acrylonitrile, methyl acrylate or styrene.

U.S. Pat. No. 3,697,640 relates to materials such as medicaments and nutrients for ruminants which are coated with nitrogen-containing cellulosic materials such as, for example, cellulose propionate morpholino butyrate. U.S. Pat. No. 3,988,480 relates to a proteinaceous feedstuff for ruminants which has been treated with acetic acid to render it rumen stable.

U.S. Pat. No. 3,383,283 relates to coating pharmaceutical pellets with a plurality of charges of fatty acid as a melt or in solution. The fatty acid may then be dusted with a fine inert powder such as talc.

U.S. Pat. No. 3,275,518 relates to a tablet coating composition comprising a film-forning resin or plastic and a hard water-soluble or water-dispersible substance. Stearic acid is mentioned as an optional water-insoluble wax which may be included as an additive. Additional materials such as dyes, pigments, water-insoluble waxes, plasticizing agents, etc., may also be added to the coating.

U.S. Pat. No. 3,623,997 relates to a method of sealing polymeric material walls of minute capsules by treating the capsules with a waxy material.

U.S. Pat. No. 3,073,748 relates to tablets coated with a solution of an amphoteric film-forming polymer. The polymer is described as one selected from the group consisting of copolymer of (a) vinylpyridines with (b) a lower aliphatic, a,B-unsaturated monocarboxylic acid of 3 to 4 carbon atoms and copolymers of (a), (b) and a neutral comonomer selected from the group consisting of methyl acrylate, acrylonitrile, vinyl acetate, methyl methacrylate and styrene.

British Pat. No. 1,217,365 and Canadian counterpart No. 851,128 relate to a particulate feed additive composition for ruminants wherein each particle comprises one or more amino acids totally encased in a continuous film of protective material which is transportable through the rumen without substantial degradation therein but which releases the active substance posterior to the omasum. Suggested as protective materials are fatty acid triglycerides such a hydrogenated vegetable and animal fast, waxes such as rice-brand wax, and resin wax blends which are emulsified and/or dissolved in the intestinal tract.

Also of interest is U.S. Pat. No. 4,060,598 which relates to coated tablets prepared by applying to a core of active material a coating composition made up of a film forming aqueous synthetic resin dispersion and a water or alkaline soluble material.

This invention describes binary coating compositions comprised of a polymer and at least one inorganic substance which are suitable for rumen-stable preparation of nutrients and medicaments such a methionine, glucose, and lysine.

DESCRIPTION OF THE INVENTION

In accordance with this invention, coating compositions which comprise a physiologically acceptable, pH-senstive, film-forming polymeric substance and an inorganic substance or mixture of inorganic substances dispersed throughout the polymeric material are provided. These coating compositions are resistant to environmental conditions of the rumen but release the core material under the environmental conditions of the abomasum and/or intestine and are particularly suitable for rumen-stable preparations of cores containing nutrients or medicaments.

The polymeric substances which are useful in the coatings of this invention include those which, in combination with the inorganic substance described hereinafter, are physiologically acceptable and resistant to a pH of greater than about 5 but capable of releasing the core of the pellets at a pH of less than about 3.5, at the normal body temperature of ruminants (37° C.). The polymeric substances include polymers, copolymers and mixtures of polymers, and/or copolymers having basic amino groups in which the nitrogen content of the polymeric substance is between about 2 and about 14% and typical weight average molecular weights of 90,000 or more. The polymeric substances are of sufficient molecular weight to have film-forming properties when the polymer is deposited from a solution and after removal of a solvent, dispersing medium or on cooling from a melt. Polymeric substances having the characteristics defined herein include certain modified natural polymers, homo- and interpolymers obtained by addition polymerization methods, homo- and copolymers obtained by condensation polymerization methods and mixtures thereof. The polymeric material is comprised of at least one polymer, copolymer, or blend of polymers (herein sometimes collectively referred to as polymer or polymeric substance) selected from the group consisting of cellulose derivatives such as cellulose propionate morpholinobutyrate; polymer containing addition-type monomeric moieties such as acrylonitrile, vinylated derivatives of pyridine, styrene, methylstyrene, and vinyl toluene; esters and amides of methacrylic acid or acrylic acid such as a dialkylamino ethyl acrylate or methacrylate in which the alkyl group contains from 1 to 6 carbon atoms; polymerizable ethylenically unsaturated aliphatic hydrocarbon monomers such as ethylene, propylene or butadiene; vinyl esters such as vinyl acetate, vinyl propionate or vinyl stearate; vinyl esters such as methyl, ethyl, propyl or stearyl, vinyl substituted heterocyclic ring or condensed ring compounds containing basic nitrogen configurations such as vinyl carbazole, vinyl quinoline, N-vinylpyrrole and 5-vinyl pyrozoline; polymer of the condensation-type wherein a diacid such as phthalic, terephthalic, or succinic is combined with a polyfunctional alcohol to form polyesters wherein either the acid or glycol moiety may contain basic nitrogen not reactive in the polymerization process but reactive to variable pH environments and wherein the same or similar diacids may be reacted with polyfunctional amines to form polyamide-type polymers containing basic nitrogen not reacted in the polymerization process; and other basic nitrogen containing polymers such as preformed polymers which have been formed by reacting an existing polymer with a nitrogen containing organic or inorganic moiety such as polybutadiene to which ammonia has been reacted with the remaining double bond. Especially preferred are poly(vinylpyridine), polymeric derivatives of vinylpyridine, and the copolymers of the various isomers and derivatives of vinylpyridine copolymerized with one or more of the above-mentioned addition-type monomers. Many of these polymers are commercially available. They can be prepared by conventional techniques well known in the art.

Also, especially preferred are cellulose propionate morpholinobutyrate, and polymers, copolymers, and blends of polymers selected from the group consisting of vinylpyridine, styrene, acrylonitrile, methacrylate, and methylmethacrylate. Most especially preferred are the copolymers of vinyl pyridine and styrene, e.g., 2-vinylpyridine/styrene copolymer (about 65/35).

The inorganic substances are selected from, for example, alkaline earth fatty acid salts, clays, silicates, silicon oxides, metallic flake material, and alkaline earth carbonates. Alkaline earth fatty acid salts include, for example, calcium stearate, magnesium stearate, and the like. Inorganic clays include, for example, talc, bentonite, kaolin and zeolite. Inorganic silicates include, for example, magnesium silicate. Alkaline earth carbonates include, for example, calcium carbonate and magnesium carbonate. Metallic flake materials include, for example, aluminum flake. Silicon oxides include, for example, silicon dioxide. The amount of inorganic substances in the coating is from about 20% to about 84% of the coating weight.

The inorganic substances may be treated by comminutation to reduce the particle size and to increase the dispersibility in the coating so as to further improve the effectiveness of the coating. The comminutation can be carried out by any means for crushing or reducing the particle size of the inorganic substance. Such mean can be by ball milling, grinding, and the like. The particle size of at least 15% of the particles should be less than 5 microns, and 85% of the particles less than 10 microns. The specified sizes are measurements at the largest dimension, e.g., largest diameter if a sphere or platelet.

One preferred method for comminutation is to ball mill the inorganic substance. A preferred ball mill useful in the practice of this invention comprises a cylindrical container mounted horizontally and partially filled with ceramic balls. Surface modification of the flake material in acetone is accomplished by rotating the ball mill and its contents about the horizontal axis of the mill at a rate sufficient to lift the balls to one side and then cause them to roll, slide, and tumble (cascade) to the lower side.

A laboratory procedure practiced in this invention is described as follows:

1. Weigh approximately 570 g of ceramic balls and add these balls into a ball mill. The total volume of the balls is approximately 15–25% of the volume of the cylindrical container.
2. Add 137 g of a mixture of flake material and 320 mL acetone to the ball mill and seal the container to minimize evaporation of acetone during the operation.
3. Rotate the ball mill on a roller at a speed of ~90 rpm for about 16 hr.
4. Decant the contents and wash the container and balls with acetone. The dispersion is ready to be used for the preparation of a coating dope, or the dispersion is dried by evaporating acetone at 50° C. The dry product is then redispersed into a polymer solution to make a coating dope.

Pellet cores are formed from a material which is beneficial to the host ruminant upon passing through the rumen and entering the abomasum and/or intestine. Such material can be drugs or antibiotics, sugars, proteins, starches, amino acids, and the like.

One method for preparing the cores is to make a dough of the core material and extrude the dough into cylindrical pellets. The pellets are then rounded by rolling or other suitable means and dried to remove the water or diluent used in forming the dough.

The pellets are then coated. One convenient means for coating the pellets is by contacting them with the coating material in a suitable solvent or mixture of solvents. The polymeric material may conveniently be dissolved in the solvent, which should by physiologically acceptable in the event there are residues upon evaporation of the solvent. The inorganic substance is then blended in the solution. The coating material may be applied by any convenient means such as dipping, spraying, etc. The coating material forms a continuous film around the cores by the evaporation of the coating solvent. The coating is continued until the desired coating weight is obtained. Suitable coating apparatus is disclosed in U.S. Pat. No. 4,117,801.

This invention can be further illustrated by the following examples of preferred embodiments thereof, although it will be understood that these examples are included merely for purposes of illustration. When the inorganic particular material in the examples is described as ball-milled, it is meant that at least 15% of the particles are less than 5 microns and at least 85% are less than 10 microns.

EXAMPLE 1

A mixture of about 450 g lysine.HCl (90 wt %) and 50 g microcrystalline cellulose (10 wt %) is thoroughly blended and then mixed with about 110 g water. The moisture content of the dough is adjusted to about 18% water. The wet dough is then extruded and pelletized by using an extruder equipped with a 2-in. diameter die and a rotating chopper blade at the die face. The die openings are 1.6 mm in diameter and the chopper blade is controlled to produce short cylindrical rods with a length to diameter ratio of about 1 to 1.5. The wet, raw pellets are rounded or polished to an average aspect ratio of about 1.3. The rounded pellets are then dried to a water content of 1% or less.

A portion of the dried pellets is coated to a coating weight of about 14 wt % with a coating composition containing 60 wt % 2-vinylpyridine/styrene (80/20) copolymer and 40 wt % ball milled talc. The ball milled talc is prepared by ball milling talc with 50% of the particles having a number average particle diameter of 10μ for 24 hr in a ball mill to obtain talc having a reduced average particle size in the specified range (15% less than 5μ0 and 85% less than 10μ). A Coulter counter is used to determine the particle size distribution.

A sample of the coated pellets is extracted in synthetic buffered rumen test fluid for 24 hr at 39° C. The supernatant is analyzed for lysine.HCl by using an X-ray emission spectroscopic method.

The in vitro rumen-protection value is determined as percent protection of total amino acid in the pellets after 24 hr. The following equation is used for the calculation of percent protection:

$$\% \text{ protection} = \left(1 - \frac{\text{concentration of amino acid in the extract}}{\text{total amino acid in the pellet sample}}\right) \times 100.$$

The rumen protection of the sample of coated pellets is greater than 90%.

Other portions of the dried pellets are coated to a coating weight of about 12 and 10% with the same coating composition used in the 14% coating. The rumen protection of these coated pellets is about 85% and 70%, respectively.

The rumen stable pellet samples are then placed in synthetic abomasal test fluid for one hour at 39° C. The extracts are analyzed by the X-ray emission spectroscopic method. The release values are calculated from the following equation:

$$\% \text{ abomasal release} = \left(1 - \frac{\text{concentration of amino acid in the extract}}{\text{total amino acid in the pellet sample}}\right)$$

The percent of release of the rumen stable pellets in the abomasal fluid is about (93%).

This example shows that a two-component coating composed of copolymer and 40% by weight ball milled talc provides good rumen protection and excellent abomasum release.

EXAMPLE 2

(Control)

A mixture of about 450 g lysine.HCl (90 wt %) and 50 g microcrystalline cellulose (10 wt %) is thoroughly blended and then mixed with water, extruded, rounded or polished, and dried according to Example 1.

The dried pellets are coated to a coating weight of about 14 wt % with a coating composition containing 60 wt % 2-vinylpyridine/styrene (80/20) copolymer and about 40 wt % talc with 50% of the particles having an average particle size of about 10 μ or more.

A sample of the coated pellets is placed in rumen test fluid for 24 hr at ambient temperature. The rumen protection of the coated pellets is only about 15%. These rumen stable pellets are then placed in abomasal test fluid for one hour at ambient temperature. The percent of release of the rumen stable pellets in the abomasum test fluid is 92%.

This example shows that the two-component coating containing only 40% talc which had not been ball milled at a coating weight of only 14% provides pellets having very poor rumen stability and delivered only about 12% of the original highly water-soluble amino acid in abomasal fluid.

EXAMPLE 3

A mixture of about 450 g lysine.HCl (90 wt %) and 50 g microcrystalline cellulose (10 wt %) is thoroughly blended and then mixed with water, extruded, pelletized, rounded or polished, and dried according to Example 1.

The dried pellets are coated to a coating weight of about 14% with a coating composition containing about 31.5% 2-vinylpyridine/styrene (65/35) copolymer and about 68.5 wt % ball milled talc.

A sample of the coated pellets is placed in rumen test fluid for 24 hr at ambient temperature. The rumen protection of the coated pellets is about 85%, and abomasum release is greater than 90%.

This example shows the two-component coatings using about 70 wt % ball milled talc have excellent rumen stability.

EXAMPLE 4

(Control)

A mixture of about 450 g lysine.HCl (90 wt %) and 50 g microcrystalline cellulose (10 wt %) is thoroughly blended and then mixed with water, extruded, pelletized, rounded or polished, and dried according to Example 1.

The dried pellets are coated to a coating weight of about 14% with a coating composition containing about 31.5% 2-vinylpyridine/styrene (65/35) copolymer and about 68.5 wt % talc used in Example 2.

A sample of the coated pellets is placed in rumen test fluid for 24 hr at ambient temperature. The rumen protection of the coated pellets is only about 20%.

This example shows that a two-component coating with talc which has not been ball milled provides poor rumen protection compared with that obtained with ball milled talc.

EXAMPLE 5

A mixture of about 450 g glucose (90 wt %) and 50 g microcrystalline cellulose (10 wt %) is thoroughly blended and then mixed with water, extruded, pelletized, rounded or polished, and dried according to Example 1.

The dried pellets are coated to a coating weight of about 14% with a coating composition containing 31.5% 2-methyl-5-vinylpyridine/styrene (80/20) copolymer and 68.5% ball milled talc of Example 1.

A sample of the coated pellets is placed in rumen test fluid for 24 hr at ambient temperature. The rumen protection of the coated pellets is about 90–95% and abomasum release is greater than 90%.

This example shows that 2-methyl-5-vinylpyridine/styrene copolymer can be used in place of the 2-vinylpyridine/styrene copolymer.

Similar results are obtained using other inorganic clays such as bentonite kaolin, or mica in place of talc.

This example also shows that cores of highly water-soluble substances other than amino acids can be coated with the two-component coating to provide rumen stable pellets.

EXAMPLE 6

A mixture of about 450 g methionine (90 wt %) and 50 g binders composed of compressible sugar (6% by wt), sodium carboxymethyl cellulose (4% by wt) is blended and then mixed with water, extruded, pelletized, rounded or polished, and dried according to Example 1.

The dried pellets are coated to a coating weight from about 4.5% to about 14% with a coating composition containing about 31.5% 2-methyl-5-vinylpyridine/styrene (80/20) copolymer and about 68.5 wt % talc or ball milled talc of Example 1.

The rumen protection and abomasal release of the coated pellets are compared in the following table.

| % Coating | % Protection | | % Release | |
|---|---|---|---|---|
| | Talc, | [Talc]* | Talc, | [Talc]* |
| 5 | 30 | 85 | 94 | 90 |
| 8 | 64 | 92 | 90 | 93 |
| 11 | 82 | 96 | 89 | 87 |
| 14 | 89 | 98 | 86 | 86 |

*[Talc]: Ball milled talc.

EXAMPLE 7

A mixture of about 400 g lysine.HCl (80 wt %) and 100 g methionine (20 wt %) is thoroughly blended and then mixed with water, extruded, pelletized, rounded or polished, and dried according to Example 1.

The dried pellets are coated to a coating weight of about 14% with a coating composition containing 20% 2-vinylpyridine/styrene (70/30) copolymer and 80 wt % talc with and without ball mill treatment.

A sample of the coated pellets from each preparation is placed in rumen test fluid for 24 hours at 39° C. The lysine protection of the coated pellets containing talc without ball mill treatment in the coating is about 10%, but the lysine protection is about 75% for the coated pellets containing ball milled talc in the coating.

EXAMPLE 8

A mixture of about 450 g methionine (solubility less than 5 g per 80 g water at 20° C.) (90 wt %) and 50 g microcrystalline cellulose (10 wt %) is thoroughly blended and then mixed with about 110 g water. The moisture content of the dough is adjusted to about 13.8% water. The wet dough is then extruded and pelletized by using an extruder equipped with a 2-in diameter die and a rotating chopper blade at the die face. The die openings are 1.6 mm in diameter and the chopper blade is controlled to produce short cylindrical rods with a length to diameter ratio of about 1 to 1.5. The wet, raw pellets are rounded or polished to remove the sharp corners and edges. The rounded pellets are then dried to a water content of 1% or less.

A portion of the dried pellets are coated to a coating weight of about 14 wt % with a coating composition containing 31.5 wt % 2-vinylpyridine/styrene (80/20) copolymer and 68.5 wt % ball milled talc.

The rumen protection of the sample of coated pellets is about 90% and abomasum release is greater than 90%.

Other portions of the dried pellets are coated to a coating weight of about 12 and 10% with the same coating composition used in the 14% coating. The rumen protection of these coated pellets is about 85% and 70%, respectively.

The rumen stable pellets are then placed in synthetic abomasal test fluid for 1 hr at 30° C. The percent of release of the rumen stable pellets in the abomasum was about 93%.

EXAMPLE 9

The dried pellets prepared according to Example 8 are coated to a coating weight of about 15 wt % with a coating composition containing 80 wt % 2-vinylpyridine/styrene (80/20) copolymer and about 20 wt % ball milled talc.

A sample of the coated pellets is placed in rumen test fluid for 24 hr at 39° C. The rumen protection of the coated pellets is about 90%. These rumen stable pellets are then placed in abomasal test fluid for 1 hr at 39° C. The percent of release of the rumen stable pellets in the abomasum test fluid is 78% with 22% of the pellets remaining undissolved.

This example shows that the two-component coating containing only 20% talc at a coating weight of 14% provides pellets having good rumen stability and good abomasum release.

EXAMPLE 10

The dried pellets according to Example 8, are coated to a coating weight of about 8% with a coating composition containing 31.5% 2-vinylpyridine/styrene (80/20) copolymer and 68.5 wt % calcium stearate. Fifteen percent of the particles of calcium carbonate is less than 5 micron and 85% is less than 10 microns.

A sample of the coated pellets is placed in rumen test fluid for 24 hr at 39° C. The rumen protection of the coated pellets is about 90–95% and abomasum release is greater than about 90%.

This example shows that using calcium stearate in place of talc provides a coating which at only 8% coating weight provides excellent rumen stability even when 50% less coating material is used.

In Examples 11–14 which follow, 15% of the inorganic particles is less than 5 microns and 85% is less than 10 microns.

EXAMPLE 11

The dried pellets, according to Example 8, are coated to a coating weight of about 14% with a coating composition containing 31.5% 2-methyl-5-vinylpyridine/styrene (80/20) copolymer and 68.5 wt % of particulate calcium carbonate.

A sample of the coated pellets is place in rumen test fluid for 24 hr at 39° C. The rumen protection of the coated pellets is about 85% and abomasum release is greater than 90%.

This example shows that calcium carbonate can be used in place of talc and provides similar results.

EXAMPLE 12

The dried pellets, according to Example 8, are coated to a coating weight of about 14% with a coating composition containing 31.5% 2-methyl-5-vinylpyridine/styrene (80/20) copolymer and 68.5% of particulate bentonite.

A sample of the coated pellets is placed in rumen test fluid for 24 hr at 39° C. The rumen protection of the coated pellets is about 90% and abomasum release is greater than 90%.

Similar results are obtained using other inorganic clays such as kaolin in place of bentonite.

EXAMPLE 13

The dried pellets, according to Example 1, are coated to a coating weight of about 14% with a coating composition containing 31.5% 2-methyl-5-vinylpyridine/styrene (80/20) copolymer and 68.5% of particulate silicon dioxide.

A sample of the coated pellets is placed in rumen test fluid for 24 hr at 39° C. The rumen protection of the coated pellets is about 90-95% and abomasum release is greater than 90%.

EXAMPLE 14

The dried pellets, according to Example 8, are coated to a coating weight of about 14% with a coating composition containing 31.5% 2-methyl-5-vinylpyridine/styrene (80/20) copolymer and 68.5% of particulate magnesium silicate.

A sample of the coated pellets is placed in rumen test fluid for 24 hr at 39° C. The rumen protection of the coated pellets is about 90-95% and abomasum release is greater than 90%.

EXAMPLE 15

(Control)

The dried pellets, according to Example 8, are coated to a coating weight of about 12% with a coating composition containing 31.5% 2-vinylpyridine/styrene (80/20) copolymer and 68.5% calcium chloride.

A sample of the coated pellets is placed in rumen test fluid for 24 hr at 39° C. The rumen protection of the coated pellets is only about 20%.

EXAMPLE 16

(Control)

The dried pellets, according to Example 8, are coated to a coating weight of about 12% with a coating composition containing 31.5% 2-vinylpyridine/styrene (80/20) copolymer and 68.55 calcium sulfate.

A sample of the coated pellets is placed in rumen test fluid for 24 hr at ambient temperature. The undissolved pellets are removed from the test fluid, dried, and weighed. The rumen protection of the coated pellets is only about 20%.

EXAMPLE 17

The dried pellets, according to Example 8, are coated to a coating weight of about 12% with a coating composition containing 31.5% 2-vinylpyridine/styrene (80/20) copolymer and 68.5% magnesium stearate.

A sample of the coated pellets is placed in rumen test fluid for 24 hr at 39° C. The rumen protection of the coated pellets is about 70%.

EXAMPLE 18

(Control)

The dried lysine.HCl-containing pellets, according to Example 1, are coated to a coating weight of about 12% with a coating composition containing 31.5% 2-vinylpyridine/styrene (80/20) copolymer and 68.5 wt % calcium stearate (particle size greater than that of the present invention).

A sample of the coated pellets is placed in rumen test fluid for 24 hr at 39° C. The rumen protection of the coated pellets is only about 20%.

EXAMPLE 19

A mixture of about 450 g phenylalanine (solubility of less than 2 g per 100 cc water at 20° C.) (90 wt %) and 50 g microcrystalline cellulose (10 wt %) is thoroughly blended and then mixed with about 110 g water. The moisture content of the dough is adjusted to about 18% water. The wet dough is then extruded, pelletized, rounded or polished, and dried according to Example 1.

The dried pellets are coated to a coating weight of about 12% with a coating composition containing 31.5% 2-methyl-5-vinylpyridine/styrene (80/20) copolymer and 68.5% particulate bentonite.

A sample of the coated pellets is placed in rumen test fluid for 24 hr at 39° C. The rumen protection of the coated pellets is about 90-95% and abomasum release is greater than 90%.

Similar results are obtained using other inorganic clays such as kaolin in place of bentonite.

EXAMPLE 20

A mixture of about 450 g leucine (solubility less than 3 g per 100 cc water at 20° C.) (90 wt %) and 50 g microcrystalline cellulose (10 wt %) is thoroughly blended and then mixed with about 110 g water. The moisture content of the dough is adjusted to about 18% water. The wet dough is then extruded, pelletized, rounded or polished, and dried according to Example 1.

The dried pellets are coated to a coating weight of about 12% with a coating composition containing 31.5% 2-methyl-5-vinylpyridine/styrene (80/20) copolymer and 68.5% particulate silicon dioxide.

A sample of the coated pellets is placed in rumen test fluid for 24 hr at 39° C. The rumen protection of the coated pellets is about 90-95% and abomasum release is greater than 90%.

EXAMPLE 21

A mixture of about 450 g tryptophan (solubility less than 2 g per 100 cc water at 20° C.) (90 wt %) and 50 g microcrystalline cellulose (10 wt %) is thoroughly blended and then mixed with about 110 g water. the moisture content of the dough is adjusted to about 18% water. The wet dough is then extruded, pelletized, rounded or polished, and dried according to Example 1.

The dried pellets are coated to a coating weight of about 12% with a coating composition containing 31.5% 2-methyl-5-vinylpyridine/styrene (80/20) copolymer and 68.5% particulate silicon dioxide.

A sample of the coated pellets is placed in rumen test fluid for 24 hr at 39° C. The rumen protection of the coated pellets is about 90–95% and abomasum release is greater than 90%.

EXAMPLE 22

The dried pellets, according to Example 1, are coated to a coating weight of 14% based on total pellet weight with a coating composition containing 31.5% 2-vinylpyridine/styrene (80/20) copolymer and 68.5% particulate aluminum flake. A sample of the coated pellets is placed in a rumen test fluid for 24 hours at 39° C. The rumen protection is about 82%, and release in abomasum test fluid is about 92%.

EXAMPLE 23

The dried pellets, according to Example 8 are coated to a coating weight of 12% based on total pellet weight with a coating composition containing 30% 2-vinylpyridine/styrene (80/20) copolymer and 70% particulate aluminum flake. A sample of the coated pellets is placed in a rumen test fluid for 24 hours at 39° C. The rumen protection is 93%, and release in abomasum test fluid is about 90%.

In Examples 17 and 19–23, 15% of the particles of inorganic material is less than 5 microns and 85% is less than 10 microns.

Whenever the term "inherent viscosity" (I.V.) is used in this application, it will be understood to refer to viscosity determinations made at 25° C. using 0.50 gram of polymer per 100 ml of a solvent composed of 60 wt % phenol and 40 wt % tetrachloroethane.

Unless otherwise specified, all parts, percentages, ratios, etc., are on a weight basis.

The invention has been described in detail with particular reference to preferred embodiment thereof, but it will be understood that variations and modifications can be effected within the spirit and scope of the invention.

We claim:

1. A composition adapted for use as a coating material for pellets orally administerable to ruminants which protects the core of said pellets in the rumen and releases it postruminally consisting essentially of
    (a) a physiologically acceptable film-forming polymeric substance comprising a polymer, copolymer or mixture thereof having basic amino groups, the nitrogen content of which constitutes between about 2 and about 14% by weight of the polymeric substance, and
    (b) an inorganic particulate material dispersed throughout said polymeric substance, at least 15% of the inorganic particulate material having a size of less than about 5 microns and at least 85% of the inorganic particular material having a size of less than 10 microns, said inorganic material accounting for about 20–84% of the total composition weight.

2. A composition according to claim 1 wherein said polymeric substance is a copolymer comprising repeat units from vinylpyridene.

3. A composition according to claim 2 wherein said vinylpyridene is 2-vinylpyridene.

4. A composition according to claim 1 wherein said polymeric substance is a copolymer comprising repeat units from 2-vinylpyridene and styrene.

5. A composition according to claim 4 wherein the ratio of repeat units of 2-vinylpyridene to styrene is about 65:35.

6. A composition according to claim 1 wherein said inorganic particulate material is selected from alkaline earth fatty acid salts, inorganic clays, inorganic silicates, silicon oxides, and alkaline earth carbonates.

7. A composition according to claim 1 wherein said inorganic particulate material is selected from calcium stearate, magnesium stearate, talc, bentonite, kaolin, zeolite, magnesium silicate, calcium carbonate, magnesium carbonate, and silicon dioxide.

8. A composition adapted for use as a coating material for pellets orally administerable to ruminants which protects the core of said pellets in the rumen and releases it postruminally consisting essentially of
    (a) a physiologically acceptable film-forming polymeric substance comprising a polymer, copolymer or mixture thereof having basic amino groups, the nitrogen content of which constitutes between about 2 and about 14% by weight of the polymeric substance, and
    (b) an inorganic particulate material dispersed throughout said polymeric substance, at least 15% of the inorganic particulate material having a size of less than about 5 microns and at least 85% of the inorganic particulate material having a size of less than 10 microns, said inorganic particulate material being selected from the group consisting of alkaline earth fatty acid salts, inorganic silicates, silicon oxides and alkaline earth carbonates, said inorganic material accounting for about 20–84% of the total composition weight.

9. A composition adapted for use as a coating material for pellets orally administerable to ruminants which protects the core of said pellets in the rumen and releases it postruminally consisting essentially of
    (a) a physiologically acceptable film-forming polymeric substance comprising a polymer, copolymer or mixture thereof having basic amino groups, the nitrogen content of which constitutes between about 2 and about 14% by weight of the polymeric substance, and
    (b) an inorganic particulate material dispersed throughout said polymeric substance, at least 15% of the inorganic particulate material having a size of less than about 5 microns and at least 85% of the inorganic particulate material having a size of less than 10 microns, said inorganic particulate material being selected from the group consisting of calcium stearate, magnesium stearate, bentonite, kaolin, zeolite, magnesium silicate, calcium carbonate, magnesium carbonate and silicon dioxide, said inorganic material accounting for about 20–84% of the total composition weight.

10. A pellet adapted for oral administration to a ruminant comprising a core material beneficial to a ruminant postruminally and a coating over the core material consisting essentially of the composition of claim 1.

11. A pellet adapted for oral administration to a ruminant comprising a core material beneficial to a ruminant postruminally and a coating over the core material consisting essentially of the composition of claim 2.

12. A pellet adapted for oral administration to a ruminant comprising a core material beneficial to a ruminant postruminally and a coating over the core material consisting essentially of the composition of claim 4.

13. A pellet adapted for oral administration to a ruminant comprising a core material beneficial to a ruminant postruminally and a coating over the core material consisting essentially of the composition of claim 6.

14. A pellet adapted for oral administration to a ruminant comprising a core material beneficial to a ruminant postruminally and a coating over the core material consisting essentially of the composition of claim 7.

15. A pellet adapted for oral administration to a ruminant comprising a core material beneficial to a ruminant postruminally and a coating over the core material consisting essentially of the composition of claim 8.

16. A pellet adapted for oral administration to a ruminant comprising a core material beneficial to a ruminant postruminally and a coating over the core material consisting essentially of the composition of claim 9.

* * * * *

UNITED STATES PATENT AND TRADEMARK OFFICE
CERTIFICATE OF CORRECTION

PATENT NO. : 4,780,315

DATED : October 25, 1988

INVENTOR(S) : Stephen H. W. Wu and Edward G. Miller, Jr.

It is certified that error appears in the above-identified patent and that said Letters Patent is hereby corrected as shown below:

Column 13, line 57, Claim 1(b), "inorganic particular material having a size of less" should read ---inorganic particulate material having a size of less---

Column 13, line 63, Claim 2, "units from vinylpyridene" should read ---units from vinylpyridine---

Column 13, line 65, Claim 3, "vinylpyridene is 2-vinylpyridene" should read ---vinylpyridine is 2-vinylpyridine---

Column 13, line 68, Claim 4, "units from 2-vinylpyridene and styrene" should read ---units from 2-vinylpyridine and styrene---

Column 14, line 2, Claim 5, "ratio of repeat units of 2-vinylpyridene to styrene is" should read ---ratio of repeat units of 2-vinylpyridine to styrene is---

Signed and Sealed this

Seventh Day of March, 1989

Attest:

DONALD J. QUIGG

*Attesting Officer*  *Commissioner of Patents and Trademarks*